United States Patent [19]

Gallant

[11] Patent Number: 4,782,831

[45] Date of Patent: Nov. 8, 1988

[54] VOLUME-CONTROLLED MANUAL RESUSCITATOR

[76] Inventor: John H. Gallant, 432 High St. East, Strathroy, Ontario, Canada, N7G 1H5

[21] Appl. No.: 54,707

[22] Filed: May 27, 1987

[30] Foreign Application Priority Data

May 27, 1986 [CA] Canada .................................. 510134

[51] Int. Cl.$^4$ .............................................. A61M 16/00
[52] U.S. Cl. ............................ 128/264.18; 128/205.24
[58] Field of Search ...................... 128/205.14, 205.13, 128/204.18, 205.24, 207.14, 207.16

[56] References Cited

U.S. PATENT DOCUMENTS

| | | | |
|---|---|---|---|
| 2,711,170 | 6/1955 | Bornstein | 128/205.24 |
| 3,090,380 | 5/1963 | Dold | 128/205.13 |
| 3,548,821 | 12/1970 | Gigauri et al. | 128/205.14 |
| 3,754,550 | 8/1973 | Kipling | 128/205.24 |
| 3,933,171 | 1/1976 | Hay | 128/205.24 |
| 3,964,476 | 6/1976 | Palleni | 128/205.13 |
| 4,176,663 | 12/1979 | Hewlett | 128/205.24 |
| 4,351,329 | 9/1982 | Ellestad et al. | 128/205.24 |
| 4,567,889 | 2/1986 | Lehmann | 128/205.24 |

FOREIGN PATENT DOCUMENTS 782326 4/1968 Canada .

Primary Examiner—Edward M. Coven
Assistant Examiner—Timothy G. Philips
Attorney, Agent, or Firm—Cushman, Darby & Cushman

[57] ABSTRACT

A manual resuscitator is disclosed, comprising a plenum chamber, a pressure chamber communicating with the plenum chamber via a main inflow valve, and a cylindrical chamber within the pressure chamber, communicating with the pressure chamber via holes in the cylinder wall. The plenum chamber receives ambient air or has oxygen-enriched air flowing through. An outflow tube leads from the pressure chamber to a patient connector. The cylindrical chamber houses an adjustable platform for adjusting the volume of the chamber via a threaded volume adjustment rod. A balloon inside the cylindrical chamber is sealingly connected to an external bulb. The outflow tube includes a Puritan Bennett valve modified to function as a Fink valve, and includes a connection for a P.E.E.P. system.

5 Claims, 2 Drawing Sheets

VOLUME-CONTROLLED MANUAL RESUSCITATOR

BACKGROUND OF THE INVENTION

This invention relates to manual resuscitators, and specifically to a manual resuscitator with control on tidal volume.

When spontaneous breathing has halted, the easiest method to reestablish breathing is through the application of mouth to mouth resuscitation. This is not always the most desirable method to use, and consequently a number of devices have been manufactured to manually ventilate a patient. The devices, commonly called manual resuscitators, consist essentially of an inflatable bug or reservoir, a face-mask or endotracheal tube connector, and connections between the reservoir and the mask. The resuscitators are either open to the air or attached to an oxygen enriched supply. The face mask is placed over the patient's nose and mouth, the reservoir is squeezed and gas is forced down the tube and into the patient's lungs. Once the operator stops squeezing the reservoir and releases the pressure, the patient exhales automatically and the reservoir assumes its original shape, drawing in gas for the next inflation. The process is then repeated. The resuscitators are adapted so that if the patient begins to breathe spontaneously, the resuscitator will not hinder this function.

The capacity of existing adult resuscitator reservoirs is typically between 1500 to 2000 cc, paediatric reservoirs from 600–750 cc, and infant reservoirs around 200 cc. Existing resuscitators generally are used and constructed in such a manner that the only indicators as to how much gas is being forced out of the reservoir and into the patient's lungs are the degree to which the patient's chest rises when the reservoir is squeezed, and the resultant back pressure felt by the squeezing hand.

The formula for calculating the average respiratory tidal volume is 10 ml of gas for every 1 kg of body weight. Using this formula, 700 ml would be the approximate tidal volume required for a 70 kg adult. Adult lungs are generally strong and resilient and consequently if too much gas is forced into the lungs few side effects will be observed. The lungs of a generally healthy 70 kg adult likely would not be seriously injured if a tidal volume as high as 2000 ml was used.

There is an acute problem in the case of infants, however, especially premature infants. Premature infants not only have less lung development than full term infants, and smaller tidal volumes, but also are far more likely to require resuscitation. Using the above formula, a 1 kg infant should have a tidal volume of about 10 ml, and in practice, about 10 to 16 ml is typical for a premature infant weighing about 1 kg. If the only mechanism for controlling the amount of gas delivered is squeezing the reservoir to varying degrees, it is extremely difficult for a clinician to administer 10–16 ml of gas from a reservoir with a capacity of 200 cc. Administering too much gas to the infant could very possibly rupture the lungs, causing the condition known as pneumothorax. This condition is frequently observed in infants who have been resuscitated using a manual resuscitator and then paced on an automatic ventilator. (The automatic ventilator has been blamed for this condition, but an increasing number of clinicians believe the condition may be caused by over-inflation of the lungs during manual resuscitation.)

Control of tidal volume is generally desireable in resuscitation, but is particularly desireable in the case of infant resuscitation. There are extremely few infant resuscitators on the market, and generally there are no controls of tidal volume. There are many adult resuscitators on the market, but generally they too have no controls of tidal volume.

It should be understood that although this invention is intended primarily for manual resuscitators for infants, it could be applied just as easily to manual resuscitators for adults, although there the need is not as great.

SUMMARY OF THE INVENTION

It is an aim of the present invention to provide clinicians with an improved manual resuscitator.

It is a further aim of the present invention to provide the clinician with a manual resuscitator which offers control of tidal volume of gas introduced into a patient's lungs.

Thus in accordance with the present invention there is provided a manual resuscitator comprising a first chamber for patient gas or air, having check valve inlet means, and outflow means for leading to a patient. A second chamber, including means for adjusting its volume, communicates with the first chamber. A balloon is within the second chamber, and large enough to fill the second chamber when inflated. A squeezable bulb external to the chambers is sealingly connected to the balloon. Thus when the bulb is squeezed, the balloon inflates to fill the second chamber, thereby displacing gas into the first chamber, whereby a volume of gas proportional to the volume of displaced gas is delivered to the patient via the outflow means.

Further features of the invention will be described or will become apparent in the course of the following detailed description.

BRIEF DESCRIPTION OF THE DRAWINGS

In order that the invention may be more clearly understood, the preferred embodiment thereof will now be described in detail by way of example, with reference to the accompanying drawings, in which.

Figure 1:
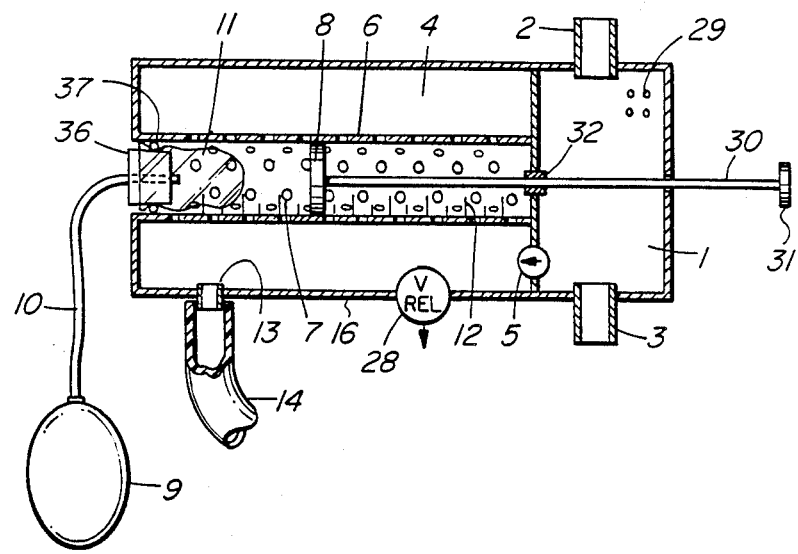
FIG. 1 is a top view of the preferred embodiment of the resuscitator.

DETAILED DESCRIPTION OF THE PREFERRED EMBODIMENT (a) Structure

The preferred embodiment of the invention is a device comprising three chambers, namely a plenum chamber 1, a desirably transparent pressure chamber 4 communicating with the plenum chamber via a main inlet check valve 5, and a transparent cylindrical chamber 6 within the pressure chamber, communicating with the pressure chamber via holes 7 in the cylinder wall. There are many such holes 7 positioned around and along the cylinder wall. The chamber 6 may be formed from stainless steel mesh. The plenum chamber 1 receives ambient air or oxygen enriched gas via a connection 2. The gas flows through the plenum chamber 1 and out an outlet 3. Outlet 3 desirably has a one-way check valve so that gases cannot return through it. The bottom of the plenum chamber is provided with small condensate drain holes 29 to drain any moisture which condenses from the gas entering the plenum chamber.

An outflow tube 14 leads from an outlet 13 in the wall of the pressure chamber 4 to a patient connector, as will be described in greater detail below.

The connection 2 is a standard fitting to which the output from a gas source which includes a heater/nebulizer may be connected, so that heated and humidified gas can be supplied to the patient. In conventional manual resuscitators, no such standard fitting is usually supplied, so that it is not possible to heat and humidify the gas being supplied. In the case of oxygen enriched gas, this of course means that the patient is receiving relatively cold and very dry gas. Since the time on manual resuscitation is limited, this may not be a significant problem in the case of adults. However, in the case of infants, the airway and lung passages, which are very small, can be dried out very quickly, and it would be much better to supply heated and humidified gas even for only very short time periods.

The cylindrical chamber 6 houses an adjustable platform 8, resembling a piston, for adjusting the volume of the chamber 6. A threaded volume adjustment rod 30 terminating in a knob 31 passes through a threaded opening 32 in the wall of the pressure chamber 4 at its inner. A wax seal or other suitable means (not shown), such as a fairly long threaded portion in the threaded opening 32, should be used to prevent leakage through the threads. Graduations 12 on the wall of the cylindrical chamber enable the operator to adjust the platform 8 to a position which will ensure that a desired volume of gas will be delivered towards the patient's lungs, by turning the adjustment knob 31 to position the platform 8 as desired. A balloon, bellows, piston, or rolling diaphragm (a balloon 11 is illustrated) is attached to the inside of the cylindrical chamber 6, and is sealed against the wall of the cylindrical chamber 6 by the operation of a plug 36 and O-ring 37 between the plug and wall which retains the balloon 11 in position. The balloon 11 is connected via a tube 10 to a bulb 9 which lies outside the device. The gas in the balloon-bulb circuit does not come into contact with the gas which circulates in the cylindrical and pressure chambers.

An adjustable pop-off valve 28 is provided on the wall 16 of the pressure chamber 4 as a safety device for venting to ambient in the event that the pressure chamber 4 is accidentally overpressured, for example if an inappropriately large volume has been selected. This valve is a conventional spring-on-disk type of valve, the spring tension being adjustable by screw means (not shown).

A minimum dead space Puritan Bennett valve 22 modified to function as a so-called Fink valve (the Fink modification of a Stephen-Slater valve) is installed in the outflow tube 14 near the distal end. The modification is effected by running a valve actuation tube 15 from the top of the Puritan Bennett valve 22 down to the outflow tube 14. The Puritan Bennett valve is modified to function as a Fink valve, instead of using the Fink modification of a Stephen-Slater valve, because it is considerably lighter in weight and because it has considerably less dead space. The valve actuation tube 15 has an inner diameter much smaller than that of the outflow tube 14, and terminates at the top of the modified Puritan Bennett valve in that valve's "collector valve" 17, which in the case of the Puritan Bennett valve is in the form of a balloon inflatable against a seat 23. The outflow tube 14 ends in a mask or endotracheal tube connector 18 (hereinafter referred to as the patient connector), which is placed onto the airway of the patient by way of a mask or endotracheal tube (not shown). Exhalation ports 19 on the distal side of the modified Puritan Bennett valve 22 open to the outside air when the collector valve 17 is deflated, so that the patient can exhale. The exhalation ports are occluded by the collector valve 17 when it is inflated against its seat 23.

A P.E.E.P. (Positive End Expiratory Pressure) accessory 20 may be connected to the valve actuation tube 15 via a check valve 21 which permits flow only in the direction from the PEEP accessory 20 to the valve actuation tube 15. When the PEEP system is in use, an adjustable independent air supply from a controlled source of gas under pressure forces air into the valve actuation tube 15 so that during the exhalation cycle, the collector valve 17 is kept partially pressurized, so that a corresponding positive end expiratory pressure is maintained, further exhalation being prevented by the collector valve 17 occluding the exhalation ports 19. The check valve 21 prevents gas flowing down the valve actuation tube 15 during the inspiration cycle from being diverted from the collector valve 17 and flowing towards the PEEP accessory 20 when the PEEP option is not being used. The PEEP accessory 20 can be set so that the collector valve 17 is inflated to varying degrees, thus controlling the PEEP by allowing the gas to escape from the circuit and the patient's lungs only down to the desired PEEP level, representing an increase in functional residual capacity of the lungs. This is accomplished by varying the flow rate of the gas from the independent supply, and observing the PEEP shown on the pressure gauge 50 described below. A bleed hole 35 is provided close to the check valve 21 so that the constant flow to the one way valve doesn't completely close the exhalation port by overinflation of the collector valve 17, and to provide for more precise control of the PEEP since supply line pressure is much higher than the desired PEEP.

Two check valves are provided in the outflow tube 14 in the region of the modified Puritan Bennett valve. One check valve 25 is positioned on the device side of the valve actuation tube 15, to improve the operation of the PEEP system by preventing flow from the PEEP system down the valve actuation tube and back the outflow tube 14. The second check valve 26 is positioned on the distal side of the valve actuation tube 15, to prevent exhaled breath from entering the system.

A pressure tap 49 may be taken from the patient connector 18 downstream of the check valve 26, and is connected to a pressure gauge 50 to provide a reading of pressure there.

In adjusting the position of the platform 8, the clinician must take into account the anticipated compressible volume loss, which is determined by the so-called compliance factor of the overall device. Thus in order to deliver a specified volume of gas to the patient, a slightly larger volume of gas must be displaced by the balloon 11, taking into account the compressible volume loss. In order to minimize the compliance factor and thus the anticipated compressible volume loss, the volume of the whole apparatus including pressure chamber 4 and the outflow tube 14 leading to the patient should be kept as small as practically possible.

To keep the volume of the outflow tube 14 as small as possible, and to at the same time reduce the number of tubes being routed to the patient, coaxial routing of the various tubes is one approach which could be adopted, and which is preferable. For simplicity of illustration, such routing is not depicted in the accompanying drawings, but essentially would be as follows. The PEEP system air supply tube would be routed down to the outflow tube 14, through its wall, and thence back towards the pressure chamber through the outflow tube, there exiting the outflow tube for connection to the independent air supply. Similarly, the tube from the pressure tap would be routed through the outflow tube 14 back towards the device.

(b) Operation

The volume of gas to be introduced into the lungs is selected, allowing for the anticipated compressible volume loss, by adjusting the position of the platform 8 in the cylindrical chamber 6 by means of the adjustment knob 31. The bulb 9 is squeezed by hand. When the bulb 9 is compressed the balloon 11 inflates to fill the selected volume of the cylindrical chamber 6, displacing the gas in the cylindrical chamber into the pressure chamber 4 through the holes 7. (Many holes 7 are provided, so that the inflating balloon cannot occlude all of them to prematurely block further displacement of gas; also, as is obvious, the balloon 11 and bulb 9 must be large enough to be able to fill the cylindrical chamber 6 at its maximum volume setting). The increase in gas pressure in the pressure chamber 4 resulting from the displacement closes the main air in-flow valve 5. A volume of gas corresponding to the displaced volume, i.e. the adjusted volume of the cylindrical chamber 6, is forced into the outflow tube 14 which leads to the patient. The volume delivered corresponds to the volume displaced in accordance with the overall compliance factor for the device.

Gas flowing down the outflow tube 14 splits at the junction of the outflow tube with the valve actuation tube 15. Gas in the valve actuation tube 15 inflates the collector valve 17 occluding the exhalation ports 19. The only pathway for the pressurized gas in the outflow tube 14 is into the patient's lungs through the patient connector 18.

When the operator ceases to compress the bulb 9, it actively draws back the volume of air used to inflate the balloon 11, due to the bulb's reshaping properties. The balloon 11 is the cylindrical chamber 6 deflates, thus reducing pressure in the cylindrical chamber 6 and pressure chamber 4. The main inflow valve 5 reopens, allowing gas to flow into the pressure chamber 4 from the plenum chamber 1. With no positive pressure and flow maintained in the outflow tube 14, the collector valve 17 deflates through the valve actuation tube 15 and out through the exhalation ports 19, which thus open to permit gas to escape from the patient's lungs.

It is not strictly essential to the invention that the cylindrical chamber 6 be positioned within the pressure chamber 4, as long as there is some connection between the two which permits gas to be displaced from the cylindrical chamber into the pressure chamber. It should also be appreciated that the "cylindrical" chamber 6 need not in fact be cylindrical; in the preferred embodiment, a cylindrical shape has been selected for convenience, but that shape is by no means essential.

Figure 2:
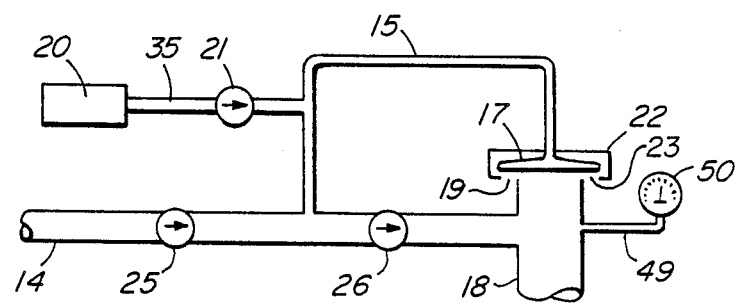
FIG. 2 is a schematic view of the outflow means and associated details.
Figure 3:
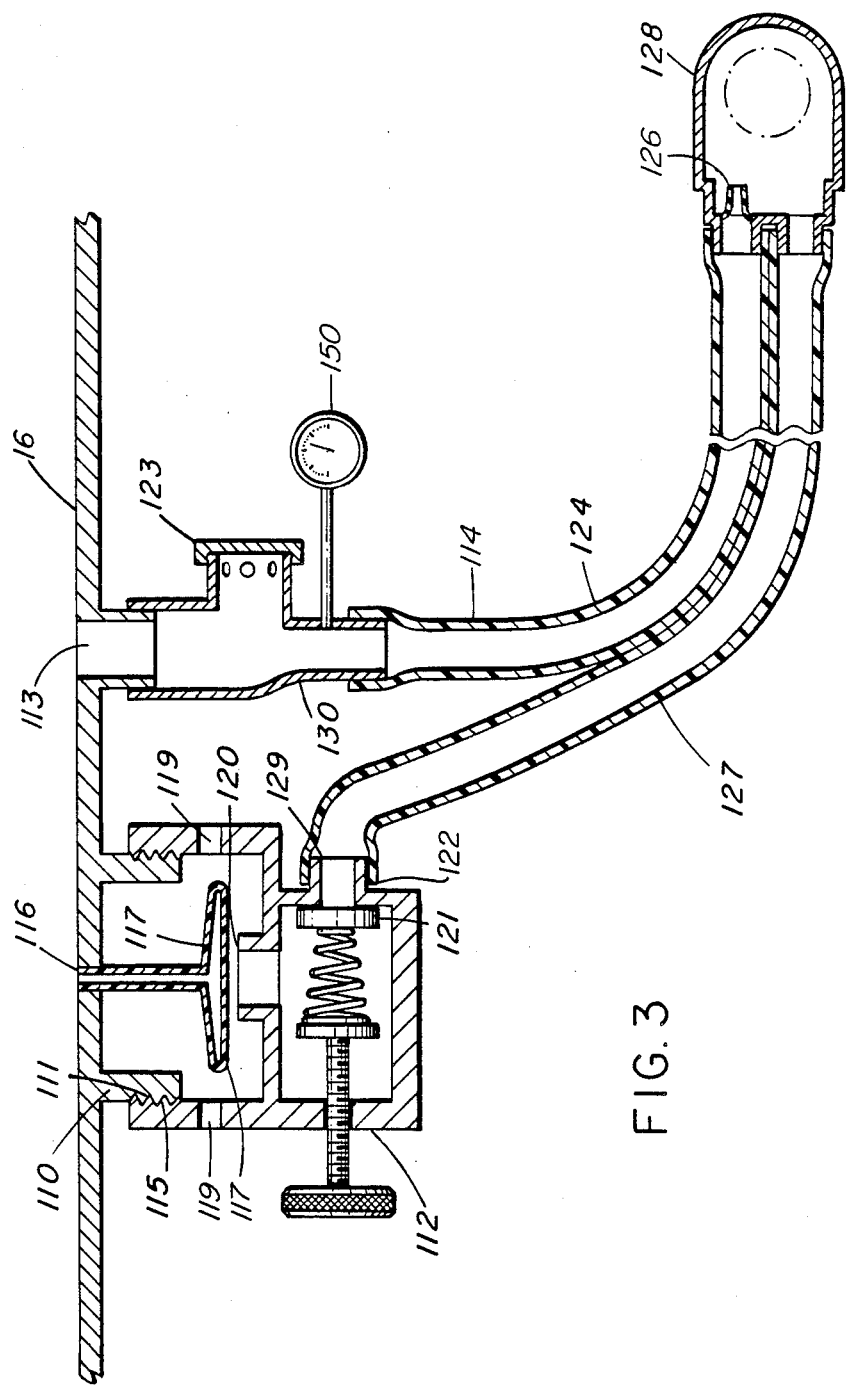
FIG. 3 is a schematic view of a second embodiment.

A modification of the embodiment of FIGS. 1 and 2 is shown in FIG. 3. In the Figure, substantially all of the apparatus of FIG. 2 is secured to and forms part of the wall 16 of the chamber 4.

Integral with or secured to the wall 16 is a cylindrical extension 110, threaded on its outside at 111, to which there is threaded a housing 112, which will be described in detail below. Also extending through the wall 16 of the chamber 4 is a gas outlet 113 corresponding to the outlet 13 of FIG. 1.

The housing is internally threaded at 115 to mate with the threads 111 on the cylindrical extension 112. It contains the P.E.E.P valve, as shown. Through a bore 116 in the wall of the chamber 4, gas can flow to the exhalation balloon 117 which, on expansion, can obturate an opening 120 defining a valve seat. An adjustable, spring loaded valve 121 is provided downstream of the opening 120. Regulation of the valve 121 by rotation of the knurled handle varies the pressure of the valve element 121 against the seat 122.

From the outlet 113 in the wall of the chamber 4 there extends a conduit to which there may be attached a manometer 150, and which has a release valve, or pop-off valve 123 which will release gases in the event of inadvertant overpressure.

Downstream of the valve 123 and downstream of the outlet there is connected a patient circuit, which may be a unitary disposable element formed from a suitable thermoplastic comprising a dual conduit formed into a Y at its proximal end for connection to the outlet 129 of the PEEP valve and extension 130 downstream of valve 123. The connector includes an outflow or gas supply branch 124 having a one-way valve 126 and a return branch 127. A typical patient connector 128, is provided to which there may be attached a mask or endotracheal tube (not shown).

In operation, upon actuation of the bulb 9 the sequence is much the same as that of FIG. 2. The increase of pressure in the chamber 4 causes the balloon 117 to expand, closing the opening 120. Thus, gas cannot flow out through the openings 119. On the other hand, gas can flow through outlet 113 to the tube 124, out through the one-way valve 126 and then to the patient. The volume of gas is precisely measured, in the same way as in the embodiment of FIG. 1. Upon exhalation, the valve 126 closes, and the exhaled gas flows back through the second branch 127 of the Y, and meets a slight resistance at the PEEP valve as described. Of course, the exhalation valve 117 has been deflated and permits the exhaled gas to flow out through the openings 119 past the seat 120.

The embodiments of the invention in which an exclusive property or privilege is claimed are defined as follows:

1. A manual resuscitator comprising:
   a first chamber for patient gas or air;
   check valve inlet means for receiving gas or air into said first chamber;
   outflow means connected to and leading from said first chamber for connection to a patient;
   a second chamber communicating with said first chamber;
   means for adjusting the volume of said second chamber;
   a balloon within said second chamber; and
   a squeezable bulb external to said chambers and sealingly connected to said balloon;
   whereby when said bulb is squeezed, said balloon inflates to fill said second chamber, thereby displacing gas from said second chamber into said first chamber, whereby a volume of gas proportional to the volume of displaced gas may be delivered to the patient via said outflow means.

2. A manual resuscitator as recited in claim 1, in which said means for adjusting the volume of said second chamber comprises a piston-like member within said second chamber and defining one wall thereof, and means for adjusting the position of said piston-like member.

3. A manual resuscitator as recited in claim 1, which said second chamber is disposed within said first chamber.

4. A manual resuscitator as recited in claim 1, further comprising a plenum chamber connected to said first chamber via said check valve inlet means, said plenum chamber having an inlet for receiving ambient air or supplied gas, and an outlet for said air or gas.

5. A manual resuscitator comprising:
(i) a chamber for receiving patient gas;
(ii) a one-way valve leading from a source of gas and operatively connected to said chamber;
(iii) a piston-like element defining one wall of said chamber, and means for adjusting the position of said piston-like element within said chamber and for securing said piston-like element in place to control the volume of said chamber;
(iv) an inflatable element within said chamber and manually operated means to inflate said element to fill said chamber and thereby displace a measured volume of gas therefrom; and
(v) means for supplying the measured volume to a patient.

* * * * *